United States Patent [19]

Lewis et al.

[11] Patent Number: 5,403,828
[45] Date of Patent: Apr. 4, 1995

[54] PURIFICATION OF CYCLODEXTRIN COMPLEXES

[75] Inventors: Larry N. Lewis; Chris A. Sumpter, both of Scotia, N.Y.; Erick V. Sprenne, Griffith; Allan R. Hedges, Crown Point, both of Ind.; Matthew L. Romberger, Macungie, Pa.

[73] Assignee: American Maize-Products Company, Hammond, Ind.

[21] Appl. No.: 196,732

[22] Filed: Feb. 15, 1994

Related U.S. Application Data

[63] Continuation of Ser. No. 928,575, Aug. 13, 1992.

[51] Int. Cl.$^6$ .............. A61K 31/70; A61K 31/71; A61K 31/715; C08B 37/16
[52] U.S. Cl. ........................ 514/58; 536/103
[58] Field of Search ................. 514/58; 536/103

[56] References Cited

U.S. PATENT DOCUMENTS

| | | | |
|---|---|---|---|
| 4,228,160 | 10/1980 | Szejtli et al. | 536/103 |
| 4,638,058 | 1/1987 | Brandt et al. | 536/103 |
| 4,668,626 | 5/1987 | Kobayashi et al. | 435/95 |
| 4,675,395 | 6/1987 | Fukazawa et al. | 536/103 |
| 4,727,064 | 2/1988 | Pitha | 514/58 |
| 4,738,923 | 4/1988 | Ammeraal | 435/97 |
| 4,748,237 | 5/1988 | Rohrbach et al. | 536/103 |
| 5,024,998 | 6/1991 | Bodor | 514/58 |
| 5,025,073 | 6/1991 | Lewis et al. | 528/15 |
| 5,070,081 | 12/1991 | Majid et al. | 514/58 |
| 5,106,939 | 4/1992 | Sumpter et al. | 528/15 |
| 5,120,720 | 6/1992 | Pitha et al. | 536/103 |
| 5,132,385 | 7/1992 | Sumpter et al. | 528/15 |
| 5,134,127 | 7/1992 | Stella et al. | 514/58 |
| 5,206,025 | 4/1993 | Courteille et al. | 424/439 |

*Primary Examiner*—Ronald W. Griffin
*Attorney, Agent, or Firm*—Lucas & Just

[57] ABSTRACT

A method is provided for purifying crude inclusion complexes of cyclodextrin which is used as a host material, in combination with a guest material, such as light mineral oil. After the crude cyclodextrin complex is formed in an aqueous media, the moisture content of the crude cyclodextrin complex is substantially reduced before it is washed with a wash solvent to substantially eliminate uncomplexed guest molecules.

10 Claims, No Drawings

PURIFICATION OF CYCLODEXTRIN COMPLEXES

This application is a continuation of application Ser. No. 07/928,575, filed Aug. 13, 1992.

This invention relates to cyclodextrins and, more particularly, to a method for purifying a cyclodextrin complex to remove uncomplexed guest molecules.

Cyclodextrins, also called "Schardinger's dextrins", cycloamyloses, cyclomaltoses and cycloglucans, are oligomers of anhydroglucose, bonded together by alpha 1,4 bonds to form a ringed compound. A six membered ring is called alpha cyclodextrin; seven, beta cyclodextrin, and eight, gamma cyclodextrin. These six, seven and eight member rings are also referred to as cyclomaltohexaose, cyclomaltoheptaose and cyclomaltoctaose, respectively.

Conventionally, cyclodextrins are obtained by treating a starch slurry with enzyme or acid to produce a gelatinized and liquefied slurry having a dextrose equivalent between 1 and 5. The gelatinized and liquefied starch slurry is then treated with cyclodextrin glycosyltransferase (CGT), at the appropriate pH, temperature and time for the selected CGT. The enzyme, CGT, is obtained from microorganisms such as *Bacillus macerans, B. magaterium, B. circulans, B. stearothermophilus,* and Bacillus sp. (alkalophilic) as well as others. The resulting digest from treatment of a gelatinized and liquefied starch slurry with CGT is then subjected to a separation and purification process to obtain cyclodextrins.

One of the commercially important aspects of cyclodextrins is their ability to form complexes with other chemical compounds. Physically a cyclodextrin is donut-shaped and the interior of the donut is hydrophobic. The consequence of this is that the cyclodextrin is able to form an inclusion complex with a substance less polar than water and which has an outer geometric dimension which allows it to fit into the cavity of the cyclodextrin. The guest molecule is encapsulated in whole or in part inside the cavity of the cyclodextrin. Generally, the complex is formed to change the solubility of a guest or stabilize the guest. It has also been found that the entrapment of the guest in the cyclodextrin delays or slows the release of the guest molecule for its intended purpose which is beneficial in some situations, see for example U.S. Pat. No. 4,774,329 issued Sep. 27, 1988. The term "cyclodextrin" as used in the specification and claims means not only cyclodextrin per se but also a modified cyclodextrin and a branched cyclodextrin.

The most widely used method for formation of a complex between a cyclodextrin and a guest molecule involves dissolving the cyclodextrin in a solvent with a guest molecule and collecting the precipitate that forms. Typically, water is the solvent. Other methods for forming complexes between a guest and cyclodextrin include cogrinding, ball milling and freeze drying.

Generally, cyclodextrin and a guest are combined in a 1:1 molar ratio in order to form the complex. In some instances excess of one or the other is used depending on the commercial value of the cyclodextrin and/or guest or the molecular weight of the guest. If the guest is small, two guests can fit into one cyclodextrin, while if the guest is large two cyclodextrins fit onto one guest.

One of the problems with the complexation process is that the product obtained directly after complexation, hereinafter referred to as the crude product, is generally not a pure complex of guest and cyclodextrin. Rather, the crude product from the complexation process comprises a complex of cyclodextrin and guest; uncomplexed cyclodextrin, uncomplexed guest; and some solvent. It is fairly common for some of the guest to either not form a complex at all with cyclodextrin, or to merely be associated with the exterior of the complex or uncomplexed cyclodextrin. In some applications, the presence of uncomplexed guest in the crude product is not detrimental; however, in other cases, it can be detrimental. For example, in the pharmaceutical field where the guest is generally the active pharmaceutical compound, exact dosages and the rate of release of the guest are important. Another example is the field of polymer chemistry where an initiator or catalyst is complexed with the cyclodextrin. In such applications, it is often imperative that the complex be devoid of uncomplexed guest. Generally, the presence of uncomplexed cyclodextrin is inconsequential because of the inert nature of cyclodextrin. There is a need to find a method for removing uncomplexed guest from the crude product without removing complexed guest from the complex.

Applicants have now discovered that an uncomplexed guest can be removed from crude product thereby purifying the crude product by washing the crude product with a wash solvent wherein said wash solvent is an organic compound that is a liquid at a temperature between about 0° C. to about 60° C., has a boiling point at a temperature between about 40° C. to about 130° C., and wherein said uncomplexed guest is soluble in said wash solvent at about 25° C. Additionally, the wash solvent should not form a complex with the uncomplexed cyclodextrin, and should not solubilize to any appreciable degree either the uncomplexed cyclodextrin or the complex. Further, the wash solvent should not cause the guest to leave the complex to any appreciable degree. It will be appreciated by those of skill in the art that any organic solvent that is able to solubilize the uncomplexed guest at 25° C. will also have a tendency to also solubilize the complexed guest. Naturally, this tendency must be minimized.

After washing, the washed product is dried to obtain a dried, purified product. The dried, purified product is substantially free of uncomplexed guest.

It is both surprising and unexpected that the wash solvent is able to carry away the uncomplexed guest molecule while leaving the complex intact, i.e. the complexed guest molecule is not removed from the complex.

The crude product from the complexation process must be recovered first, prior to the purification process of the present invention. Where the complex is formed in a solvent process, the crude product forms a precipitate and is recovered in a conventional manner such as filtration or decanting. Then, the recovered crude product is dried, if need be, in a conventional manner to a moisture of below about 50% by weight and more preferably below about 15%. Good results with respect to drying have been obtained by vacuum filtering using about 25 mm of mercury at room temperature, about 20° C. to about 25° C. Standard vacuum equipment has been used. It will be appreciated by those of skill in the art that the general recovery process for any crude product, no matter what the complexation process is, will be in the form of a filter cake, having a moisture of below about 50% by weight where the crude product is substantially free of solvent.

It is preferred that the drying step prior to the wash step be conducted in an oven to stabilize the complex. This intermediate oven drying step is conducted at a temperature below the boiling point of the guest and below about 150° C. Preferably, the temperature during the oven drying step is maintained between about 30° C. to about 150° C. and, more preferably, at about 40° C. to about 120° C. It has been found that oven drying should also be conducted at a temperature about 5° C. to about 10° C. below the boiling temperature of the guest molecule. The atmosphere during the oven drying step should be substantially free of moisture. The presence of water tends to destabilize the guest.

The washing step is accomplished either by suspending the crude product in wash solvent or by passing wash solvent through the crude product.

In passing the wash solvent through the crude product, the crude product is placed on filter paper or some other form of filter system and wash solvent is allowed to flow through the crude product. Naturally, any conventional washing process can be used wherein fine solid particles, in this case the complex, are brought into contact with a fluid and especially a liquid. In essence, this means that the solid particles are brought into contact with the wash solvent and subsequently the wash solvent and solid particles are separated.

Good results have been obtained by placing the crude product on filter paper in a vacuum funnel and pouring the wash solvent over the crude product. The amount of vacuum is preferably about 25 mm of mercury and is conducted at room temperature, about 20° C. to about 25° C. The wash solvent is also preferably at room temperature.

Alternatively, the crude product can be washed by suspending the crude product in a container of wash solvent. This is accomplished by placing the crude product into the wash solvent and then gently stirring the crude product to suspend the crude product in the wash solvent. Preferably, the wash solvent and the crude product are at room temperature. Preferably, the stirring is conducted for up to about 10 minutes and, more preferably, for about ½ minute to about 10 minutes. Good results have been obtained when the washing is conducted for about 1 to about 5 minutes. The resulting washed product is recovered from the wash container in any conventional manner using conventional equipment, and preferably by vacuum filtration. Lowering the temperature below room temperature during washing can lessen the tendency of the complexed guest to decomplex and thereby stabilize the complex, but it also generally decreases the effect of the wash solvent to wash away the uncomplexed guest. Increases in temperature during washing although tending to increase the ability of the wash solvent to wash away the uncomplexed guest, also has a tendency to decrease the stability of the complex and allow complexed guest to leave the complex. It is preferred that the washing take place at room temperature, about 20° to about 25° C.

Drying the washed product is done in any conventional manner using conventional equipment, and preferably by vacuum and at room or slightly above room temperature so as to drop the moisture content to below about 15% and preferably between about 5% and about 15%. Drying also can be done in a conventional oven at a temperature to evaporate the wash solvent without evaporating the complexed guest. Drying the washed product is done to remove the wash solvent from the product and is done without disrupting the complex or damaging the complex in any manner.

The amount of wash solvent used depends on the amount of crude product formed, and on the guest that is used to form the complex. It has been found that it is convenient to gauge the amount of wash solvent needed upon the amount of cyclodextrin used in the complexation process. Preferably, about 1 milliliter to about 40 milliliters of wash solvent are used per gram of cyclodextrin and more preferably about 5 to about 25 milliliters of wash solvent are used per gram of cyclodextrin. The term gram of cyclodextrin means the gram of cyclodextrin used initially to form the complex.

The suspension of crude product in wash solvent is the preferred means to wash the crude product if a high volume of wash solvent is necessary.

The choice of wash solvent is critical. The wash solvent must be able to solubilize the uncomplexed guest so as to remove the uncomplexed guest from the crude product without dissolving the complex itself and without removing the complexed guest from the complex. In accordance with the present invention, the wash solvent is an organic solvent and is a liquid at a temperature between about 0° C. and about 60° C., more preferably between about 10° C. and about 50° C. The wash solvent is volatile at low temperatures, between about 40° C. to about 130° C., so that it can readily be separated from the washed product without destroying the complex itself. More preferably, the wash solvent is volatile at a temperature of about 50° C. to about 80° C.

Suitable wash solvents include low molecular weight alcohols such as ethanol and methanol; low molecule weight ketones such as acetone and methyl ethyl ketone; and low molecular weight ethers such as diethyl ether and tetrahydrofuran, low molecular weight alkanes, such as hexane and methylene chloride; low molecular weight aromatics, such as toluene. Wash solvents that have been found to give good results and to fall within this category, depending on the guest molecule, are ethanol, acetone and methylene chloride.

These and other aspects of the present invention may be more fully understood with reference to the following examples:

EXAMPLE 1

This example illustrates washing a crude product containing complexes of beta cyclodextrin and the guests as listed in Table I below. Acetone was used to wash each of the crude products in Table I below except crude products No. 2 and 8. Ethanol was used for crude product No. 2 and methylene chloride was used for crude product No. 8 where COD is 1,5-cyclooctadiene.

In order to wash the crude product, the wash solvent was slowly poured over the crude product which had been placed on filter paper in a Buchner funnel. A vacuum was applied of 25 mm of mercury. The amount of wash solvent used is also in Table I below.

TABLE I

| Crude Product | Guest | Amount of Wash Solvent Used (ml/gr) |
|---|---|---|
| 1. | Diiodomethyl-p-Tolylsulfone (Amical 48) | 10.0 |
| 2. | 1-Phenyl-3-Pyrazolidone | 6.7 |
| 3. | (S)-2-Methyl-4-oxo-3-(2-propynyl)-cyclopent-2-enyl (1R)-cis, trans- | 17.0 |

TABLE I-continued

| Crude Product | Guest | Amount of Wash Solvent Used (ml/gr) |
|---|---|---|
| | chrysanthemate (ETOC) | |
| 4. | 3-Iodo-2-Propynyl Butyl Carbamate (Polyphase P-100) | 7.7 |
| 5. | Benzoyl Peroxide | 3.5 |
| 6. | N,N-Dimethylaniline | 4.4 |
| 7. | Light Mineral Oil (Conoco LTV 200) | 2.0 |
| 8. | COD Pt Cl$_2$ | 12.0 |

The amount of wash solvent used to wash the complex is based on the grams of cyclodextrin used in the complexation process, i.e. milliliters of wash solvent per gram cyclodextrin added for complexation.

In order to determine the amount of wash solvent necessary, equal amounts of crude product were washed with increasing amounts of wash solvent and the resulting washed product was assayed for guest. When subsequent assay of product washed at two different levels indicated that the guest content leveled off, then the lesser amount of wash solvent was chosen as the appropriate amount of wash solvent. The presumption is that substantially all the uncomplexed guest has been removed from the crude product when the amount of guest in the assayed complex plateaus. If no such leveling off of the guest content in the washed product is seen, then the wash solvent is actually decomplexing the guest and a different wash solvent should be selected for more effective washing.

EXAMPLE 2

This example illustrates using the intermediate drying step.

A 1:1 inclusion compound between beta cyclodextrin (BCD) and limonene was prepared as follows: BCD (10 g) was dissolved in 100 mL of water by heating to 60° C. Limonene (1.1 g) was added to the stirred homogeneous aqueous BCD solution at 60° C. and formed a top layer. A white precipitate was formed and this was collected by filtration after the limonene layer completely reacted. The solid was divided into two parts. Part A was dried in an oven at 105° C. and part B was allowed to dry on a glass fritted-funnel. Each solid was then mixed with 15 ml of acetone and then dried on glass frits to remove the acetone. $^1$H NMR showed that solid A had a BCD:limonene ratio of 0.95 and that solid B had a BCD:limonene ratio of 0.85 indicating that the brief acetone contact removed more guest from the "wet" solid B than from the "dry" solid A. The two solids were then stirred with 5 ml aliquots of either acetone or methylene chloride for 6 minutes, each containing a known amount of phenyldodecane as an internal standard. The solutions were analyzed for their limonene content by gas chromatographic analysis. As shown in Table II, dried solid A was resistant to loss of limonene upon stirring in solvent whereas wet solid B suffered considerable loss of limonene.

TABLE II

| Solid | Solvent | % mmol Limonene released |
|---|---|---|
| A | acetone | 0 |
| B | acetone | 42 |
| A | methylene chloride | 0 |

TABLE II-continued

| Solid | Solvent | % mmol Limonene released |
|---|---|---|
| B | methylene chloride | 30 |

What is claimed is:

1. A purification process for a crude product obtained from a complexation process wherein a cyclodextrin and guest are mixed and a crude product comprising a complex of cyclodextrin and guest, uncomplexed cyclodextrin and uncomplexed guest is recovered, the purification process comprising the steps of:
   (a) recovering the crude product from said complexation process;
   (b) drying the recovered crude product in an oven at a temperature below the boiling point of the guest and below about 150° C., said oven having an atmosphere which is substantially free of moisture, thereby fixing said complexed guest in said complex;
   (c) washing the recovered oven dried crude product in a washing solvent to effect the removal of uncomplexed guest, wherein said wash solvent is an organic compound that is a liquid at a temperature between about 0° C. to about 60° C., has a boiling point at a temperature between about 40° C. to about 130° C., and does not form a complex with uncomplexed cyclodextrin; and
   (d) recovering the washed product of (c) which is substantially free of uncomplexed guest molecules.

2. The process of claim 1, wherein the washing solvent is selected from the group consisting of low molecular weight alcohols, low molecular weight ketones, low molecular weight ethers, a low molecular weight alkanes, and low molecular weight aromatics.

3. The process of claim 1, wherein the cyclodextrin is selected from the group consisting of alpha cyclodextrin, beta cyclodextrin, gamma cyclodextrin, a cyclodextrin oligomer, and mixtures thereof.

4. The process of claim 2, wherein the wash solvent is selected from the group consisting of acetone and ethanol.

5. The process of claims 1, 2 or 3 wherein the washing step comprises:
   (b') suspending recovered crude product in a container of washing solvent at room temperature for a period of up to about 10 minutes, and then
   (b'') recovering the washed product from the container.

6. The process of claims 1, 2 or 3 wherein the washing step comprises:
   (b') pouring washing solvent onto the crude product which has been placed on filter paper in a vacuum funnel, and
   (b'') applying a vacuum to the crude product while pouring the washing solvent over the product to draw the washing solvent through the product.

7. The process of claims 1, 2 or 3 wherein the temperature in said oven during said drying step is between about 30° C. and about 150° C.

8. The process of claim 1, wherein the wash solvent is methylene chloride.

9. The process of claims 1, 2 or 3 wherein the temperature during the oven drying step is between about 30° C. and about 150° C. and about 5° C. to about 10° C. below the boiling point of said guest.

10. The process of claims 1, 2 or 3 wherein the temperature during the oven drying step is between about 40° C. and about 120° C. and about 5° C. to about 10° C. below the boiling point of said guest.

* * * * *

UNITED STATES PATENT AND TRADEMARK OFFICE
CERTIFICATE OF CORRECTION

PATENT NO. : 5,403,828
DATED : April 4, 1995
INVENTOR(S) : Larry N. Lewis et al.

It is certified that error appears in the above-indentified patent and that said Letters Patent is hereby corrected as shown below:

Column 3, line 53, after "washing" insert --,--;
line 55, change "has a" to --have a--.

Column 6, line 33 (claim 2), delete "a".

Signed and Sealed this

Twenty-seventh Day of June, 1995

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO.   : 5,403,828
DATED        : April 4, 1995
INVENTOR(S)  : Larry N. Lewis et al.

It is certified that error appears in the above-indentified patent and that said Letters Patent is hereby corrected as shown below:

On the title page, item [75]:

Change inventor "Erick V. Sprenne" to --Erik V. Sprenne--

Signed and Sealed this

Twelfth Day of September, 1995

Attest:

BRUCE LEHMAN

*Attesting Officer*          *Commissioner of Patents and Trademarks*